(12) United States Patent
Kato et al.

(10) Patent No.: US 6,703,201 B1
(45) Date of Patent: Mar. 9, 2004

(54) HUMAN PEC-60-LIKE PROTEIN AND DNA ENCODING THIS PROTEIN

(75) Inventors: Seishi Kato, Sagamihara (JP); Tomoko Yamaguchi, Tokyo (JP); Shingo Sekine, Sagamihara (JP); Kouju Kamata, Sagamihara (JP)

(73) Assignee: Sagami Chemical Research Center, Kanagawa (JP)

( * ) Notice: Subject to any disclaimer, the term of this patent is extended or adjusted under 35 U.S.C. 154(b) by 359 days.

(21) Appl. No.: 09/671,483

(22) Filed: Sep. 27, 2000

Related U.S. Application Data

(63) Continuation of application No. 09/065,019, filed on Apr. 17, 1998, now Pat. No. 6,280,968, application No. PCT/JP96/03061, filed on Oct. 22, 1996.

(30) Foreign Application Priority Data

Oct. 27, 1995 (JP) ............................................. 7/280272

(51) Int. Cl.$^7$ ............................ C12Q 1/68; C07H 21/02
(52) U.S. Cl. ........................... 435/6; 536/23.1; 536/24.3
(58) Field of Search ............................. 435/6; 536/23.1, 536/24.3

(56) References Cited

FOREIGN PATENT DOCUMENTS

GB        2 199 582 A        7/1988

OTHER PUBLICATIONS

National Cancer Institute, Cancer Genome Anatomy Project, GenBank Database Accession No. AA534438, Aug. 21, 1997.
Collins et al., GeneSeq Database Accession No. P80003, Nov. 6, 1990.
Metsis et al., Gen Bank Database Accession No. S46866, Jan. 5, 1993.
Church et al., GenBank Database Accession No. T12635, Jan. 5, 1994.
Bandman et al., GeneSeq Database Accession No. V38073, Sep. 14, 1998.
Bandman et al., GeneSeq Database Accession No. W62074, Sep. 14, 1998.
Laasik, J. et al., "PCE–60, A Novel Regulatory Peptide Reduces Cyclic AMP Formation In Rat Caudate Nucleus," *Biochem. Biophys, Res. Commun.* (1993) 197:849–852.
Metsis, M. et al., "Molecular cloning of PEC–60 and expression of its mRNA and peptide in the gastrointestinal tract and immune system," *J. Biol. Chem.* (1992) 267:19829–19832.
Ahren, B. et al., "The intestinal peptide PEC–60 inhibits insulin secretion in the mouse and the rat," *Pancreas* (1992) 7:443–446.
Liepinsh, E. et al., "Solution structure and dynamics of PEC–60, a protein of Kazal type inhibitor family, determined by nuclear magnetic resonance spectroscopy," *J. Mol. Biol.* (1994) 239:137–153.

Fink, E. et al., "Maino acid sequence elucidation of human acrosin–trypsin inhibitor (HUSI–II) reveals that Kazal–type proteinase inhibitors are structurally related to beta–subunits of glycoprotein hormones," *FEBS Lett* (1990) 270:222–224.
Agerberth, B. et al., "Isolation and characterization of a 60–residue intestinal peptide structurally related to the pancreatic secretory type of trypsin inhibitor; influence on insulin secretion," *Proc. Natl. Acad. Sci. USA* (1989) 86:8590–8594.
Ohmachi, Y. et al., "Expression of the pancreatic secretory trypsin inhibitor gene in the liver infected with hepatitis B virus," *J. Hepatol.* (1994) 21:1012–1016.
Ohmachi, Y. et al., "Overexpression of Pancreatic Secretory Trypsin Inhibitor in Pancreatic Cancer," *Int. J. Pancreatol* (1994) 15:65–73.
Ohmachi, Y. et al., "Specific expressionof the pancreatic–secretory–trypsin–inhibitor (PSTI) gene in hepatocellular carcinoma," *Int. J. Pancreatol* (1993) 55:728–734.
Halme, L. et al., "Concentrations of pancreatic secretory trypsin inhibitor (PSTI), acute phase proteins, and neopterin in Crohn's disease. Comparison with clinical disease activity and endoscopical findings," *Scand. J. lin. Lab. Invest.* (1993) 53:359–366.
Medl, M. et al., "TATI (tumour–associated trypsin inhibitor) as a marker of ovarian cancer," *Br. J. Cancer* (1995) 71:1051–1054.
Pectasides, D., et al., Seuarnous cell carcinoma antigen, tumor–associated trypsin inhibitor, and carcinoembryonic antigen for monitoring cervical cancer., *Am. J. Clin. Oncol.* (1994) 17:307:312.
Conlon, J.M. et al., "A peptide from the eel pancreas with structural similarity to human pancreatic secretory trypsin inhibitor," *Eur. J. Biochem* (1988) 174:149–153.
Perry, A.C. et al., "Sequence analysis of monkey acrosin–trypsin inhibitor transcripts and their abundant expression in the epididymis," *Biochimica et Biophysica Acta* (1993) 1172:159–160.
EMBL Sequences, EMBL, Heidelberg, FRG, Accession No. AA296922, Apr. 18, 1997, Adams, M.D., et al., "EST112478 retin, a II Homo sapiens cDNA 5' end similar to gastrointestinal peptide PEC–60," XP002055098.
Fuxe, K. et al., "PEC–60, a novel procine 60–residue intestinal peptide, reduces dopamine utilization in discrete parts of the neostriatum of the male rat following an intracerebroventribular injection," *Acta. Phys. Scand.* (1991) 141:139–140.
Fuxe, K. et al, "Generalized presence of a PEC–60–like peptide in catecholamine neurons," *Neuroreport* (1994) 5:1817–1821.

*Primary Examiner*—Jeffrey Fredman
(74) *Attorney, Agent, or Firm*—Fitzpatrick, Cella, Harper & Scinto

(57) ABSTRACT

The present invention provides a human PEC-60-like protein, a gastrointestinal hormone excreted by a stomach tissue and a cDNA encoding this protein. The protein and the gene of the present invention can provide a protein containing the amino acid sequence represented by Sequence No. 1 and a DNA encoding said protein exemplified as a cDNA containing the base sequence represented by Sequence No. 1 as well as a human cDNA encoding a human PEC-60-like protein and said protein by the expression of this human cDNA recombinant.

5 Claims, 1 Drawing Sheet

SEQUENCE LISTING

<160> NUMBER OF SEQ ID NOS: 3

<210> SEQ ID NO 1
<211> LENGTH: 180
<212> TYPE: DNA
<213> ORGANISM: Homo sapiens

<400> SEQUENCE: 1

```
ggaaagctcc ctttctcaag aatgcccatc tgtgaacaca tggtagagtc tccaacctgt      60
tcccagatgt ccaacctggt ctgcggcact gatgggctca catatacgaa tgaatgccag     120
ctctgcttgg cccggataaa aaccaaacag gacatccaga tcatgaaaga tggcaaatgc     180
```

<210> SEQ ID NO 2
<211> LENGTH: 398
<212> TYPE: DNA
<213> ORGANISM: Homo sapiens

<400> SEQUENCE: 2

```
gcaggcccca gccagctcag gctacactat cccaggatca gcatggccgt ccgccagtgg      60
gtaatcgccc tggccttggc tgccctcctt gttgtggaca gggaagtgcc agtggcagca     120
ggaaagctcc ctttctcaag aatgcccatc tgtgaacaca tggtagagtc tccaacctgt     180
tcccagatgt ccaacctggt ctgcggcact gatgggctca catatacgaa tgaatgccag     240
ctctgcttgg cccggataaa aaccaaacag gacatccaga tcatgaaaga tggcaaatgc     300
tgatcccaca ggagcacctc aagccatgaa gtgtcagctg gagaacagtg gtgggcatgg     360
agaggatatg acatgaaata aagatccag cccaactg                              398
```

<210> SEQ ID NO 3
<211> LENGTH: 86
<212> TYPE: PRT
<213> ORGANISM: Homo sapiens

<400> SEQUENCE: 3

```
Met Ala Val Arg Gln Trp Val Ile Ala Leu Ala Leu Ala Ala Leu Leu
 1               5                  10                  15

Val Val Asp Arg Glu Val Pro Val Ala Ala Gly Lys Leu Pro Phe Ser
                20                  25                  30

Arg Met Pro Ile Cys Glu His Met Val Glu Ser Pro Thr Cys Ser Gln
            35                  40                  45

Met Ser Asn Leu Val Cys Gly Thr Asp Gly Leu Thr Tyr Thr Asn Glu
    50                  55                  60

Cys Gln Leu Cys Leu Ala Arg Ile Lys Thr Lys Gln Asp Ile Gln Ile
65                  70                  75                  80

Met Lys Asp Gly Lys Cys
                85
```

HUMAN PEC-60-LIKE PROTEIN AND DNA ENCODING THIS PROTEIN

This is a continuation of application Ser. No. 09/065,019, now U.S. Pat. No. 6,280,968 filed Apr. 17, 1998, which is a 371 of PCT/JP96/0361 filed Oct. 1996, which is incorporated herein by reference.

APPLICATION FIELD

The present invention relates to a human PEC-60-like protein and a cDNA encoding this protein. The protein of the present invention can be used as pharmaceuticals for the treatment and diagnosis of the digestive system diseases, the immune system diseases, and the nervous system diseases, or as an antigen for preparing an antibody against said protein. The human cDNA of the present invention can be used as a probe for the gene diagnosis and a gene source for the gene therapy. Furthermore, the cDNA can be used as a gene source for large-scale production of the protein encoded by said cDNA.

PRIOR ART

PEC-60 (a peptide consisting of an N-terminal glutamic acid, a C-terminal cysteine, and 60 amino acid residues) was isolated from the pig small intestine as a protein that inhibits the glucose-induced insulin secretion from perfused pancreas [Agerberth, B. et al., Proc. Natl. Acad. Sci. USA 86: 8590–8594 (1989)]. In general, such gastrointestinal hormones are found also in the nervous systems in many cases, whereas recent immunohistological studies have revealed the localization of a putative PEC-60 in the central and peripheral catecholamine nerves [Fuxe, K. et al., Neuroreport 5: 1817–1821 (1994)]. Furthermore, it has been suggested that the peptide plays some roles in the immune system, from the observation of its existence in the peripheral blood monocyte in a high content as well as the excretion in the serum [Metsis, M. et al., J. Biol. Chem., 267: 19829–19832 (1992)].

Since PEC-60 is a multi-functional hormone acting in the digestive tract, the nervous system, the immune system, etc., as indicated above, the acquisition of a human PEC-60 leads to its utilization as medicines. Although a porcine PEC-60 cDNA has been cloned up to date [Metsis, M. et al., J. Biol. Chem., 267: 19829–19832 (1992)], any report has not been presented on the human cDNA.

DISCLOSURE OF THE INVENTION

As the result of intensive studies, the present inventors were successful in cloning of a human cDNA encoding a human PEC-60-like protein, thereby completing the present invention. That is to say, the present invention provides a protein containing the amino acid sequence represented by Sequence No. 1 that is a human PEC-60-like protein. The present invention, also, provides a DNA encoding said protein exemplified as a cDNA containing the base sequence represented by Sequence No. 1.

The protein of the present invention can be obtained, for example, by a method for isolation from human organs, cell lines, etc, a method for preparation of the peptide by the chemical synthesis on the basis of the amino acid sequence of the present invention, or a method for production with the recombinant DNA technology using the DNA encoding the human PEC-60-like protein of the present invention, wherein the method for obtainment by the recombinant DNA technology is employed preferably. For example, an in vitro expression can be achieved by preparation of an RNA by the in vitro transcription from a vector having the cDNA of the present invention, followed by the in vitro translation using this RNA as a template. Also, the recombination of the translation domain to a suitable expression vector by the method known in the art leads to the expression of a large amount of the encoded protein by using *Escherichia coli*, *Bacillus subtilis*, yeasts, animal cells, and so on.

The DNA of the present invention includes all DNA encoding said protein. Said DNA can be obtained using the method by chemical synthesis, the method by cDNA cloning, and so on.

The cDNA of the present invention can be cloned from, for example, a cDNA library of the human cell origin. The cDNA is synthesized using as a template a poly(A)$^+$ RNA extracted from human cells. The human cells may be cells delivered from the human body, for example, by the operation or may be the culture cells. A poly(A)$^+$ RNA isolated from the human stomach cancer tissue is used in Examples. The cDNA can be synthesized by using any method selected from the Okayama-Berg method [Okayama, H. and Berg, P., Mol. Cell. Biol. 2: 161–170 (1982)], the Gubler-Hoffman method [Gubler, U. and Hoffman, J. Gene 25: 263–269 (1983)], and so on, but it is preferred to use the capping method [Kato, S. et al., Gene 150: 243–250 (1994)] as illustrated in Examples in order to obtain a full-length clone in an effective manner.

The cloning of the cDNA is performed by the sequencing of a partial base sequence of the cDNA clone selected at random from the cDNA library and the search of the protein data base by the amino acid sequence predicted from the base sequence. The identification of the cDNA is carried out by determination of the whole base sequence by the sequencing, the protein expression by the in vitro translation, and the expression by *Escherichia coli*.

The cDNA of the present invention is characterized by containing the base sequence represented by Sequence No. 1, as exemplified by that represented by Sequence No. 2 possessing a 398-bp base sequence with a 261-bp open reading frame. This open reading frame codes for a protein consisting of 86 amino acid residues and possessed a signal sequence at the N-terminal end.

Hereupon, the same clone as the cDNA of the present invention can be easily obtained by screening of the human cDNA library by the use of an oligonucleotide probe synthesized on the basis of the cDNA base sequence depicted in Sequence No. 1 or Sequence No. 2.

In general, the polymorphism due to the individual difference is frequently observed in human genes. Therefore, any cDNA that is subjected to insertion or deletion of one or plural nucleotides and/or substitution with other nucleotides in Sequence No. 1 or Sequence No. 2 shall come within the scope of the present invention.

In a similar manner, any protein that is produced by these modifications comprising insertion or deletion of one or plural nucleotides and/or substitution with other nucleotides shall come within the scope of the present invention, as far as said protein possesses the activity of the protein having the amino acid sequence represented by Sequence No. 1.

The cDNA of the present invention includes cDNA fragments (more than 10 bp) containing any partial base sequence of the base sequence represented by Sequence No. 1 or No. 2. Also, DNA fragments consisting of a sense chain and an anti-sense chain shall come within this scope. These DNA fragments can be used as the probes for the gene diagnosis.

BEST MODE FOR CARRYING OUT THE INVENTION

Figure 1:
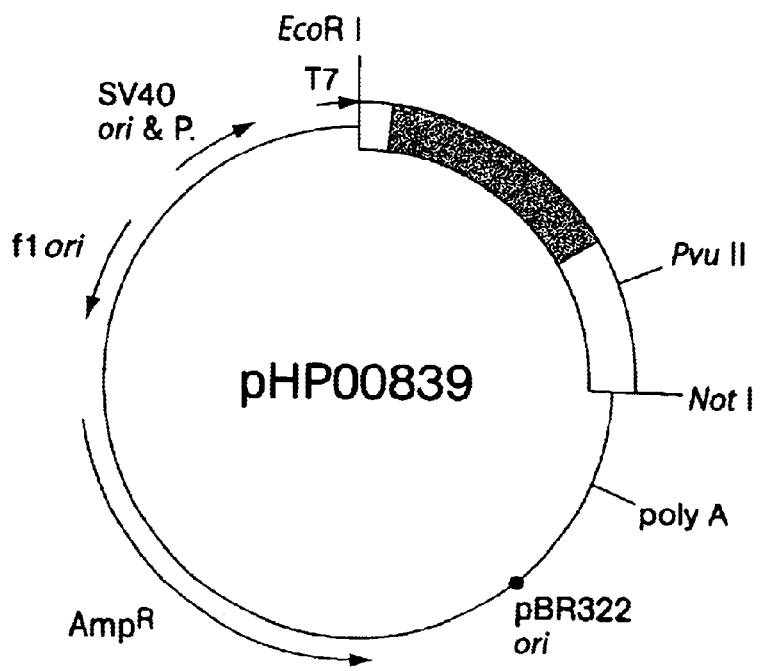
FIG. 1 is a figure depicting the structure of the plasmid pHP00839.

The present invention is embodied in more detail by the following examples, but this embodiment is not intended to restrict the present invention. The basic operations and the enzyme reactions with regard to the DNA recombination are carried out according to the literature [Molecular Cloning. A Laboratory Manual", Cold Spring Harbor Laboratory, 1989]. Unless otherwise stated, restrictive enzymes and a variety of modification enzymes to be used were those available from TAKARA SHUZO. The manufacturer's instructions were used for the buffer compositions as well as for the reaction conditions, in each of the enzyme reactions. The cDNA synthesis was carried out according to the literature [Kato, S. et al., Gene 150: 243–250 (1994)].

EXAMPLES

Preparation of Poly(A)$^+$ RNA

After 1 g of a human stomach cancer tissue was homogenized in 20 ml of a 5.5 M guanidinium thiocyanate solution, 750 μg of mRNA was prepared according to the literature [Okayama, H. et al., "Methods in Enzymology" Vol. 164. Academic Press, 1987]. This was subjected to oligo(dT)-cellulose column chromatography washed with a 20 mM Tris-hydrochloric acid buffer solution (pH7.6), 0.5 M NaCl, and 1 mM EDTA to obtain 10 μg of a poly(A)$^+$ RNA according to the literature mentioned above.

Construction of cDNA Library

Ten micrograms of the above described poly(A)$^+$ RNA were dissolved in a 100 mM Tris-hydrochloric acid buffer solution (pH 8), one unit of an RNase-free, bacterial alkaline phosphatase was added, and the reaction was run at 37° C. for one hour. After the reaction mixture was subjected to phenol extraction followed by ethanol precipitation, the pellet was dissolved in a solution containing 50 mM sodium acetate (pH 6), 1 mM EDTA, 0.1% 2-mercaptoethanol, and 0.01% Triton X-100. Thereto was added one unit of a tobacco acid pyrophosphatase (Epicentre Technologies) and a total 100 μl volume of the resulting mixture was reacted at 37° C. for one hour. After the reaction mixture was subjected to phenol extraction followed by ethanol precipitation, the pellet was dissolved in water to obtain a solution of a decapped poly(A)$^+$ RNA.

The decapped poly(A)$^+$ RNA and 3 nmol of a chimeric DNA-RNA oligonucleotide (5'-dG-dG-dG-dG-dA-dA-dT-dT-dC-dG-dA-G-G-A-3') were dissolved in a solution containing 50 mM Tris-hydrochloric acid buffer (pH 7.5), 0.5 mM ATP, 5 mM MgCl$_2$, 10 mM 2-mercaptoethanol, and 25% polyethylene glycol, whereto was added 50 units of T4RNA ligase and a total 30 μl volume of the resulting mixture was reacted at 20° C. for 12 hours. After the reaction mixture was subjected to phenol extraction followed by ethanol precipitation, the pellet was dissolved in water to obtain a chimeric-oligo-capped poly(A)$^+$ RNA.

After digestion of a vector pKA1 (Japanese Patent Kokai Publication No. 1992–117292) developed by the present inventors with KpnI, about 60 dT tails were added using a terminal transferase. A vector primer to be used below was prepared by digestion of this addition product with EcoRV to remove a dT tail at one side.

After 6 μg of the previously-prepared chimeric-oligo-capped poly(A)$^+$ RNA was annealed with 1.2 μg of the vector primer, the resulting mixture was dissolved in a solution containing 50 mM Tris-hydrochloric acid buffer (pH 8.3), 75 mM KCl, 3 mM MgCl$_2$, 10 mM dithiothreitol, and 1.25 mM dNTP (dATP+dCTP+dGTP+dTTP), 200 units of a transcriptase (GIBCO-BRL) were added, and the reaction in a total 20 μl volume was run at 42° C. for one hour. After the reaction mixture was subjected to phenol extraction followed by ethanol precipitation, the pellet was dissolved in a solution containing 50 mM Tris-hydrochloric acid buffer (pH 7.5), 100 mM NaCl, 10 mM MgCl$_2$, and 1 mM dithiothreitol. Thereto were added 100 units of EcoRI and a total 20 μl volume of the resulting mixture was reacted at 37° C. for one hour. After the reaction mixture was subjected to phenol extraction followed by ethanol precipitation, the pellet was dissolved in a solution containing 20 mM Tris-hydrochloric acid buffer solution (pH 7.5), 100 mM KCl, 4 mM MgCl$_2$, 10 mM (NH$_4$)$_2$SO$_4$, and 50 μg/ml of the bovine serum albumin. Thereto were added 60 units of an *Escherichia coli* DNA ligase and the resulting mixture was reacted at 16° C. for 16 hours. To the reaction mixture were added 2 μl of 2 mM dNTP, 4 units of an *Escherichia coli* DNA polymerase I, and 0.1 unit of an *Escherichia coli* DNase H and the resulting mixture was reacted at 12° C. for one hour and then at 22° C. for one hour.

Next, the cDNA-synthesis reaction solution was used for transformation of an *Escherichia coli* DH12S (GIBCO-BRL). The transformation was carried out by an electroporation method. A portion of the transformant was sprayed on the 2xYT agar culture medium containing 100 μg/ml ampicillin and the mixture was incubated at 37° C. overnight. A colony formed on the agar medium was picked up at random and inoculated on 2 ml of the 2xYT culture medium containing 100 μg/ml ampicillin. After incubation at 37° C. for 2 hours, the mixture was infected with a helper phage MK13KO7 (Pharmacia) and incubated further at 37° C. overnight. The culture solution was centrifuged to separate the mycelia and the supernatant, wherein a double-stranded DNA was isolated from the mycelia by the alkaline hydrolysis method and a single-stranded plasmid DNA from the supernatant according to the conventional method. After double digestion with EcoRI and NotI, the double-stranded plasmid DNA was subjected to 0.8% agarose gel electrophoresis to determine the size of the cDNA insert. On the other hand, after the sequence reaction using an M13 universal primer labeled with a fluorescent dye and a Taq polymerase (a kit of Applied Biosystems), the single-stranded phage DNA was examined with a fluorescent DNA sequencer (Applied Biosystems) to determine the about 400 bp base sequence at the 5'-terminus of the cDNA. The sequence data were filed as the Homo Protein cDNA Bank database.

CDNA Cloning

The base sequencing of the clones selected at random from the above-mentioned cDNA library was carried out and the obtained base sequence was converted to three frames of the amino acid sequence, which were subjected to a search of the protein data base. The analysis software used was GENETYX-MAC (Software Development). As the result, a protein encoded by a plasmid pHP00839 contained in the clone HP00839 was revealed to be highly homologous to the porcine PEC-60 amino acid sequence. The structure of this plasmid is depicted in FIG. 1. The structure consisting of a 42-bp 5'-nontranslation region, a 261-bp open reading frame, and a 95-bp 3'-nontranslation region (Sequence No. 2) was found from the determination of the whole base sequence of the cDNA insert. The open reading frame codes for a protein consisting of 86 amino acid residues and the search of the protein data base using this sequence revealed such a high 73.3% homology to the porcine PEC-60 amino acid sequence over the whole regions. Table 1 shows the comparison between the amino acid sequence of the human PEC-60-like protein of the present invention (HS) and that of the porcine PEC-60 (SS). Therein, the marks of * (asterisk) and ·(dot) represent an amino acid residue identical with the protein of the present invention and an amino acid residue similar to the protein of the present invention, respectively.

aenzyme, and then digested with SalI. The reaction product was subjected to 1.5% agarose gel electrophoresis, cutting-off of an about 200-bp DNA fragment from the gel, and purification.

Figure 2:
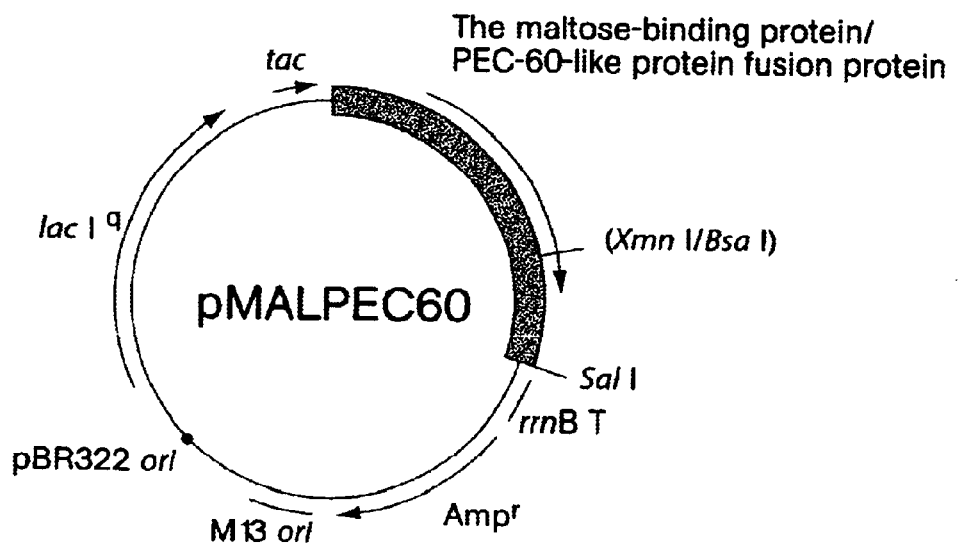
FIG. 2 is a figure depicting the structure of the *Escherichia coli* expression vector pMALPEC60 of the present invention.

Then, after 1 μg of pMALTM-c2 (New England Biolabs) was digested with 20 units of XmnI (New England Biolabs) and SalI, the product was subjected to 0.6% agarose gel electrophoresis followed by cutting-off of a 6.7-kbp DNA fragment from the gel. The vector fragment and the cDNA fragment were ligated by using a ligation kit and then *Escherichia coli* JM109 was transformed. Plasmid pMALPEC was prepared from the transformant and the objective recombinant was identified by the restriction enzyme cleavage map. FIG. 2 depicts the structure of the obtained plasmid.

A suspension of 10 ml of an overnight-incubated liquid of pMALPEC60/JM109 in 500 ml of the Rich culture medium (contains 10 g of triptone, 5 g of yeast extract, 5 g of NaCl,

TABLE 1

```
HS  MAVRQWVIALALAALLVVDREVPVAAGKLPFSRMPICEHMVESPTCSQMSNLVCGTDGLT
    ****··**.*******..*******.*.*   **********.***.**.. . ******.*
SS  MAVRLWVVALALAALFIVDREVPVSAEKQVFSRMPICEHMTESPDCSRIYDPVCGTDGVT
HS  YTNECQLCLARIKTKQDIQIMKDGKC
    *..**.******..******.***.*
SS  YESECKLCLARIENKQDIQIVKDGEC
```

Protein Synthesis by In Vitro Translation

The vector pHP00839 having the cDNA of the present invention was used for in vitro translation with a TNT rabbit reticulocyte lysate kit (Promega). In this case, [$^{35}$S] methionine was added to label the expression product with a radioisotope. Each of the reactions was carried out according to the protocols attached to the kit. Two micrograms of the plasmid pHP00839 was reacted at 30° C. for 90 minutes in a total 100 μl volume of the reaction mixture containing 50 μl of the TNT rabbit reticulocyte lysate, 4 μl of a buffer solution (attached to the kit), 2 μl of an amino acid mixture (Met-free), 8 μl of [$^{35}$S]methionine (Amersham) (0.37 Mbq/μl), 2 μl of T7RNA polymerase, and 80 U of RNasin. To 3 μl of the resulting reaction mixture was added 2 μl of the SDS sampling buffer (125 mM Tris-hydrochloric acid buffer, pH 6.8, 120 mM 2-mercaptoethanol, 2% SDS solution, 0.025% bromophenol blue, and 20% glycerol) and the resulting mixture was heated at 95° C. for 3 minutes and then subjected to SDS-polyacrylamide gel electrophoresis. Determination of the molecular weight of the translation product by carrying out the autoradiography indicated that the cDNA of the present invention yielded the translation product with the molecular mass of about 10 kDa. This value is consistent with the molecular weight of 9,454 predicted for the putative protein from the base sequence represented by Sequence No. 2, thereby indicating that the cDNA certainly codes for the protein represented by Sequence No. 2.

Expression of Fusion Protein by *Escherichia coli*

Two strands of an oligonucleotide primer PR1 (5'-GCGGTCTCGGGAAAGCTCCCTTTCTCAAG-3') and PR2 (5'-GCGTCGACTCAGCATTTGCCATCTTTCA-3') were synthesized using a DNA synthesizer (Applied Biosystems) according to the attached protocol.

PCR was carried out using 1 ng of the plasmid pHP00839 as well as 100 pmole each of primer PR1 and primer PR2 to amplify a region encoding a maturation protein consisting of C-terminal 60 amino acid residues. After phenol extraction and ethanol precipitation, the pellet was digested with 20 units of BsaI (New England Biolabs), treated with Klenow and 2 g of glucose per one liter) was incubated in a shaker at 37° C. and isopropylthiogalactoside was added so as to make 1 mM when $A_{600}$ reached about 0.5. After further incubation at 37° C. for 3 hours, the mycelia collected by centrifugation were suspended in 25 ml of a column buffer for amylose column (10 mM Tris-hydrochloric acid, pH 7.4, 200 mM NaCl, and 1 mM EDTA). After sonification, the suspension was centrifuged and the supernatant was charged into an amylose column (New England Biolabs) with a 3.5-ml head volume. After the column was washed with an 8-fold column volume of the column buffer, a maltose-binding protein/PEC60-like protein fusion protein was eluted with 20 ml of the column buffer containing 10 mM maltose to afford 15.3 mg of the fusion protein. The SDS-polyacrylamide electrophoresis of this fusion protein indicated a single band at the position of about 50 kDa. This molecular mass value is consistent with the molecular weight predicted for the maltose-binding protein/PEC60-like protein fusion protein.

To 200 μl of the column buffer containing 100 μg of the maltose-binding protein/PEC60-like protein fusion protein was added 1 μg of factor Xa and the reaction was run at 4° C. for 12 hours. The reaction solution was subjected to the amylose-column chromatography and the fraction eluted straight was collected to afford 16 μg of a PEC-60-like protein. The SDS-polyacrylamide electrophoresis of this protein indicated a band at the position of about 7 kDa corresponding to the PEC-60-like protein of the present invention.

Probable Industrial Applicability

The present invention provides a human PEC-60-like protein, a DNA encoding said protein, and a human CDNA encoding said protein. The protein of the present invention can be used as pharmaceuticals for the treatment and diagnosis of the digestive system diseases, the immune system diseases, and the nervous system diseases or as an antigen for preparing an antibody against said protein. Said DNA can be used for the expression of a large amount of said protein.

What is claimed is:

1. A hybridization probe comprising a polynucleotide sequence encoding a polypeptide comprising the amino sequence of SEQ ID NO: 3.

2. A hybridization probe according to claim 1 comprising the polynucleotide of SEQ ID NO:2.

3. A hybridization probe according to claim 1 comprising nucleotides 43 to 303 of SEQ ID NO: 2.

4. A method for detecting polynucleotides comprising nucleotides 43 to 303 of SEQ ID NO:2 in a biological sample containing nucleic acid material comprising the steps of hybridizing an oligonucleotide probe consisting of nucleotides 43 to 303 of SEQ ID NO: 2 to nucleic acid material of a biological sample and detecting a hybridization complex.

5. A method for detecting polynucleotides encoding a polypeptide comprising the amino acid sequence of SEQ ID NO: 3 in a biological sample containing nucleic acid material comprising the steps of hybridizing an oligonucleotide probe consisting of nucleotides 43 to 303 of SEQ ID NO: 2 to nucleic acid material of a biological sample and detecting a hybridization complex.

* * * * *

UNITED STATES PATENT AND TRADEMARK OFFICE
CERTIFICATE OF CORRECTION

PATENT NO.    : 6,703,201 B1
DATED         : March 9, 2004
INVENTOR(S)   : Seishi Kato et al.

It is certified that error appears in the above-identified patent and that said Letters Patent is hereby corrected as shown below:

Title page,
Item [56], References Cited, OTHER PUBLICATIONS,
"Fink E. at al., reference, "Maino" should read -- Fink, E. et al., "Amino --;
"Ohmachi, Y. et al., reference, "Specific expressionof" should read -- Ohmachi, Y. et al., "Specific expression of --; and
"Pectasides, D. et al., Seuarnous" should read -- Pectasides, D. et al., Squamous --.

Column 6,
Line 1, "aenzyme" should read -- enzyme --.

Signed and Sealed this

Third Day of August, 2004

JON W. DUDAS
*Acting Director of the United States Patent and Trademark Office*